(12) United States Patent
Taygerly

(10) Patent No.: US 8,383,824 B2
(45) Date of Patent: Feb. 26, 2013

(54) HETEROCYCLIC ANTIVIRAL COMPOUNDS

(75) Inventor: Joshua Paul Gergely Taygerly, San Francisco, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 158 days.

(21) Appl. No.: 12/950,127

(22) Filed: Nov. 19, 2010

(65) Prior Publication Data

US 2011/0123489 A1 May 26, 2011

Related U.S. Application Data

(60) Provisional application No. 61/263,350, filed on Nov. 21, 2009.

(51) Int. Cl.
| | |
|---|---|
| *C07D 213/63* | (2006.01) |
| *C07D 213/75* | (2006.01) |
| *A61K 31/4412* | (2006.01) |
| *A61P 31/12* | (2006.01) |
| *C07D 239/54* | (2006.01) |
| *C07D 253/07* | (2006.01) |
| *A61K 31/513* | (2006.01) |
| *A61K 31/53* | (2006.01) |

(52) U.S. Cl. ........................ 546/290; 514/245
(58) Field of Classification Search .................. 546/290; 514/245
See application file for complete search history.

(56) References Cited

U.S. PATENT DOCUMENTS

| | | | | |
|---|---|---|---|---|
| 6,221,335 | B1 * | 4/2001 | Foster ........................ | 424/1.81 |
| 6,440,710 | B1 * | 8/2002 | Keinan et al. ................ | 435/148 |
| 6,603,008 | B1 * | 8/2003 | Ando et al. ................ | 546/269.7 |
| 7,517,990 | B2 * | 4/2009 | Ito et al. ........................ | 546/184 |
| 2007/0082929 | A1 * | 4/2007 | Gant et al. .................... | 514/338 |
| 2007/0197695 | A1 * | 8/2007 | Potyen et al. ................ | 524/110 |
| 2010/0021423 | A1 * | 1/2010 | Brameld et al. ............. | 424/85.2 |

FOREIGN PATENT DOCUMENTS

| | | |
|---|---|---|
| WO | WO 2009/032124 A1 | 3/2009 |
| WO | WO 2010/010017 A1 | 1/2010 |
| WO | WO 2010/072598 A1 | 7/2010 |
| WO | WO 2010/111436 A2 | 9/2010 |

OTHER PUBLICATIONS

Dyck, Journal of Neurochemistry vol. 46 Issue 2, pp. 399-404 (1986).*
Tonn, Biological Mass Spectrometry vol. 22 Issue 11, pp. 633-642 (1993).*
Haskins, Biomedical Spectrometry vol. 9 Issue 7, pp. 269-277 (1982).*
Wolen, Journal of Clinical Pharmacology 1986; 26:419-424.*
Browne, Journal of Clinical Pharmacology1998; 38:213-220.*
Baillie, Pharmacology Rev.1981 ;33:81-132.*
Gouyette, Biomedical and Environmental Mass Spectrometry, vol. 15, 243-247 (1988).*
Cherrah, Biomedical and Environmental Mass Spectrometry vol. 14 Issue 11, pp. 653 -657 (1987).*
Pieniaszek, J Clin Pharmacol.1999; 39:817-825.*
Honma et al., Drug Metab Dispos 15 (4): 551 (1987).*
(International Search Report on Patentability for International Patent Application No. PCT/EP/2010/067718).
Zhang, X., "Inhibitors of hepatitis C—a review of the recent patent literature" *Idrugs* 5(2):154-158 (Jan. 1, 2002).

* cited by examiner

*Primary Examiner* — Venkataraman Balasubramanian
(74) *Attorney, Agent, or Firm* — Brian L. Buckwalter

(57) ABSTRACT

Compounds having the formula I wherein

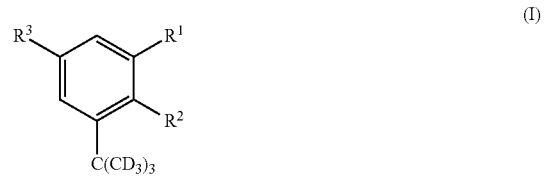

wherein $R^1$, $R^2$ and $R^3$ are as defined herein are Hepatitis C virus NS5b polymerase inhibitors with improved bioavailability. Also disclosed are compositions and methods for treating an HCV infection and inhibiting HCV replication.

16 Claims, No Drawings

HETEROCYCLIC ANTIVIRAL COMPOUNDS

CROSS-REFERENCE TO RELATED APPLICATIONS

This application claims the benefit of priority to U.S. Ser. No. 61/263,350 filed Nov. 21, 2009 which is hereby incorporated by reference in its entirety.

FIELD OF THE INVENTION

The present invention provides non-nucleoside compounds of formula I, and certain derivatives thereof, which are inhibitors of RNA-dependent RNA viral polymerase. The isotope-containing compounds encompassed by the present claims exhibit improved pharmacokinetic characteristics. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND OF THE INVENTION

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae*: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.*, 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.*, 1999 19:5; Di Besceglie, A. M. and Bacon, B. R., *Scientific American*, October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investing. Drugs* 2003 12(8):1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.-Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase. The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell in vivo and be converted in vivo to its triphosphate form to compete as a substrate at the polymerase nucleotide binding site. This conversion to the triphosphate is commonly mediated by cellular kinases which impart additional structural limitations on any nucleoside. In addition this requirement for phosphorylation limits the direct evaluation of nucleosides as inhibitors of HCV replication to cell-based assays (J. A. Martin et al., U.S. Pat. No. 6,846,810; C. Pierra et al., *J. Med. Chem.* 2006 49(22):6614-6620; J. W. Tomassini et al., *Antimicrob. Agents and Chemother.* 2005 49(5):2050; J. L. Clark et al., *J. Med. Chem.* 2005 48(17):2005).

Compounds of the present invention and their isomeric forms and pharmaceutically acceptable salts thereof are also useful in treating viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

Other interferons currently in development include albinterferon-α-2b (Albuferon), IFN-omega with DUROS, LOCTERON™ and interferon-α-2b XL. As these and other interferons reach the marketplace their use in combination therapy with compounds of the present invention is anticipated.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCHSO3034 (Broceprevir, Schering), TMC435350 (Tibotec/Medivir) and ITMN-191 (Intermune). Other protease inhibitors in earlier stages of development include MK7009 (Merck), BMS-790052 (Bristol Myers Squibb), VBY-376 (Virobay), IDXSCA/IDXSCB (Idenix), BI12202 (Boehringer), VX-500 (Vertex), PHX1766 Phenomix).

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

SUMMARY OF THE INVENTION

There is currently no preventive treatment or generally effective therapy for treating Hepatitis C virus (HCV) infections. Currently approved therapies, which exist only against HCV, have limited effectiveness and are associated with serious side effects. Design and development of new more effective therapies with less toxicity is, therefore, essential.

The present invention relates to compounds of formula I wherein:

$R^1$ is CH=CHAr, C≡CAr, $[C(R^5)_2]_2$Ar or naphthyl wherein said naphthyl is optionally substituted with $[C(R^5)_2]_{0-3}NR^aR^b$.

Ar is phenyl, pyridinyl or pyridazinyl wherein said Ar is optionally independently substituted with one to three substitutents selected from the group consisting of:
  (a) $[C(R^5)_2]_{0-3}NR^aR^b$,
  (b) $C_{1-10}$ hydroxyalkyl wherein one or two carbon atoms optionally can be replaced by oxygen provided that the replacement does not form a peroxide,
  (c) $C_{1-3}$ alkoxy-$C_{1-6}$ alkyl,
  (d) carboxyl,
  (e) $X^1$-$[C(R^5)_2]_{1-6}CO_2R^4$ wherein $X^1$ is O, $NR^5$, or a bond and $R^4$ is hydrogen or $C_{1-6}$ alkyl,
  (f) $C_{1-6}$ alkoxycarbonyl,
  (g) halogen,
  (h) $[C(R^5)_2]_{0-3}CN$,
  (i) $C_{1-6}$ alkyl, and
  (j) $C_{1-6}$ haloalkyl.

$R^2$ is hydrogen, $C_{1-6}$ alkoxy, halogen or $C_{1-6}$ alkyl.

$R^3$ is a heteroaryl radical selected from the group consisting of A-1, A-2, A-3 and A-4 said heteroaryl being optionally substituted by halogen, $C_{1-6}$ alkyl, $C_{1-3}$ haloalkyl, $C_{1-6}$ alkoxy.

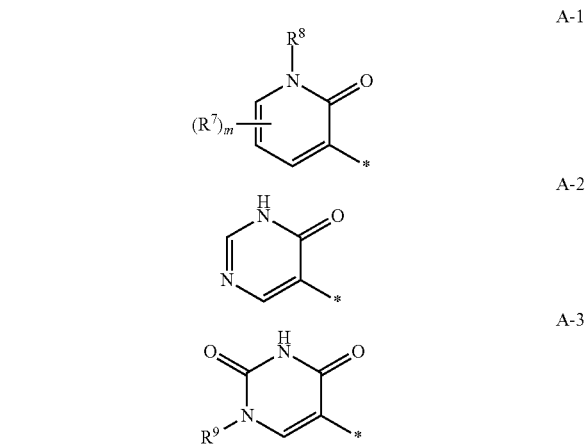

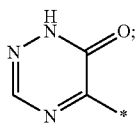

A-4

$R^5$ is independently in each occurrence hydrogen or $C_{1-3}$ alkyl.

$R^7$ is selected from the group consisting of:
(a) halogen,
(b) $C_{1-6}$ alkyl wherein one or two carbon atoms optionally can be replaced by oxygen provided that the replacement does not form a peroxide,
(c) $C_{1-3}$ haloalkyl,
(d) $C_{1-3}$ alkoxy,
(e) $C_{2-6}$ hydroxyalkyl wherein one or two carbon atoms optionally can be replaced by oxygen provided that the replacement does not form a peroxide or a hemiacetal;
(f) $NR^5[C(R^5)_2]\text{-}C_{2-6}$ hydroxyalkyl;
(g) cyano-$C_{1-3}$ alkyl,
(h) $X^2[C(R^5)_2]_{1-6}CO_2H$,
(i) $[C(R^5)_2]_{1-6}NR^cR^d$, and
(j) $X^2\text{—}[C(R^5)_2]_{2-6}NR^cR^d$ wherein $X^2$ is O or $NR^5$.

$R^8$ is hydrogen or $CH_2OR^9$ wherein $R^9$ is valine, proline or $P(=O)(OH)_2$.

$R^9$ is hydrogen or $C_{1-6}$ alkyl.

m is zero or one.

$R^a$ and $R^b$ are (i) independently in each occurrence
(a) hydrogen,
(b) $C_{1-6}$ alkyl,
(c) $SO_2R^6$ wherein $R^6$ is $C_{1-6}$ alkyl, $C_{1-6}$ haloalkyl, $C_{3-7}$ cycloalkyl, $C_{3-7}$ cycloalkyl-$C_{1-3}$ alkyl, $C_{1-6}$ alkoxy-$C_{1-6}$ alkyl or $[C(R^5)_2]_{0-6}NR^cR^d$,
(d) $C_{1-3}$ haloalkyl,
(e) $C_{1-6}$ acyl,
(f) carbamoyl,
(g) $C_{1-3}$ alkylcarbamoyl, or
(h) $C_{1-3}$ dialkylcarbamoyl,
or (ii) $R^a$ and $R^b$ taken together with the nitrogen to which they are attached are an optionally substituted cyclic amine.

$R^c$ and $R^d$ are independently hydrogen or $C_{1-6}$ alkyl or $R^c$ and $R^d$ together with the nitrogen to which they are attached are an optionally substituted cyclic amine.

The present invention further relates to pharmaceutically acceptable salts of compounds of formula I.

The present invention also provides a method for treating a disease a Hepatitis C Virus (HCV) virus infection by administering a therapeutically effective quantity of a compound according to formula I to a patient in need thereof. The compound can be administered alone or co-administered with other antiviral compounds or immunomodulators.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or „ ------ „ drawn through a bond each refer to the point of attachment of a functional group or other chemical moiety to the rest of the molecule of which it is a part. Thus, for example:

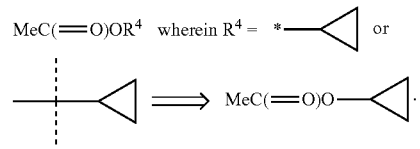

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

The compounds of formula I may contain a basic center and suitable acid addition salts are formed from acids which form non-toxic salts. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.,* 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations,* 2nd edition Wiley-VCH, New York 1999; *Comprehensive Organic Synthesis,* B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

The term "isotopologue" has been used to distinguish species that differ only in the isotopic composition thereof (IUPAC Compendium of Chemical Terminology $2^{nd}$ Edition 1997). Isotopologues can differ in the level of isotopic enrichment at one or more positions and/or in the positions(s) of isotopic enrichment.

Variations from the natural isotopic abundance can occur in a synthesized compound depending upon the source of chemical precursors used in the synthesis and form isotope exchange during the synthesis. Thus isotopic enrichment factor of each deuterium present at a site designated as a site of deuteration is independent of deuteration at other sites and some variation in the deuterium content at other then the designated sites may occur and these variations can result in the formation of isotopologues are within the scope of the compounds claimed. Deuterium enrichment factor at sites not designated as deuterium or "D" will be less than 49.5% and typically significantly less than 49.5%.

Since the natural abundance of deuterium is 0.015%, these variations from the naturally observed levels of deuterium will not have a material effect on observed biological properties of the compounds.

Unless otherwise stated, when a position is explicitly or implicitly designated as "H" or "hydrogen", the isotope ratio is presumed to have hydrogen at its natural abundance isotopic composition with the provision that some adventitious variations can result from the synthetic processes.

The term "isotopic enrichment factor" as used herein means the ratio between the isotopic abundance of D at a specified position in a compound of this invention and the naturally occurring abundance of that isotope. In one embodiment of the present invention there is provided a compound according to formula I wherein the isotopic enrichment factor of the tert-butyl moiety is at least 3300 (49.5%). To avoid any ambiguity, the isotopic enrichment factor for the tert-butyl refers to the aggregate of the three methyl groups and the methyl groups are not assessed independently.

In other embodiments, there is provided a compound according to formula I with an isotopic enrichment factor for each deuterium present at a site designated as a potential site of deuteration on the compound of at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Compounds according to formula I that inhibit HCV polymerase have been disclosed in U.S. Ser. No. 12/460,658 filed Jul. 22, 2009 which is hereby incorporated by reference in it entirety. While the hydrophobic tert-butyl substituent contributes to binding of the compounds to the polymerase, it also has been shown to be primary site for oxidative metabolism. Metabolic oxidation reduces the maximum concentration ($C_{max}$) and the concentration of the active ingredient in the systemic circulation as measured by the total area under a plot of concentration of drug vs. time (AUC). Substitution of deuterium for hydrogen in the tert-butyl substituent has now been demonstrated to significant increase $C_{max}$ and the AUC.

In one embodiment of the present invention there is provided a compound according to formula I wherein $R^1, R^2, R^3, R^4, R^5, R^6, R^7, R^8, R^9, R^a, R^b, R^c, R^d, X^1, X^2$, Ar and m are as described hereinabove.

In a second embodiment of the present invention there is provided a compound according to formula I wherein $R^1$ is CH=CHAr and $R^3$ is A-1.

In a third embodiment of the present invention there is provided a compound according to formula I wherein $R^1$ is CH=CHAr, Ar is phenyl substituted at the four-position by $NR^aR^b$ and optionally further substituted at one of the open positions, $R^2$ is $C_{1-6}$ alkoxy or hydrogen or hydrogen and $R^3$ is A-1.

In a fourth embodiment of the present invention there is provided a compound according to formula I wherein $R^1$ is CH=CHAr, Ar is phenyl substituted at the four-position by $NR^aR^b$ and optionally further substituted at one of the open positions, $R^a$ is hydrogen, $R^b$ is $SO_2R^6$ wherein $R^6$ is $C_{1-6}$ alkyl, $C_{3-7}$ cycloalkyl or $C_{3-7}$ cycloalkyl-$C_{1-3}$ alkyl, $R^2$ is $C_{1-6}$ alkoxy or hydrogen, $R^3$ is A-1 and $R^7$ is $C_{1-6}$ alkyl, $C_{1-6}$ alkoxy or halogen and m is 1.

In a fifth embodiment of the present invention there is provided a compound according to formula I wherein $R^1$ is CH=CHAr, Ar is either 2-pyridinyl substituted at the 5-position by $NR^aR^b$ or 3-pyridinyl substituted at the six-position by $NR^aR^b$, $R^a$ is hydrogen, $R^b$ is $SO_2R^6$, $R^6$ is $C_{1-6}$ alkyl, $C_{3-7}$ cycloalkyl or $C_{3-7}$ cycloalkyl-$C_{1-3}$ alkyl and $R^3$ is A-1.

In a sixth embodiment of the present invention there is provided a compound according to formula I wherein $R^1$ is naphthalene and $R^3$ is A-1.

In a seventh embodiment of the present invention there is provided a compound according to formula I wherein $R^1$ is 2-naphthalene substituted 6-position by $NR^aR^b$ wherein $R^a$ is hydrogen, $R^b$ is $SO_2R^6$, $R^6$ is $C_{1-6}$ alkyl, $C_{3-7}$ cycloalkyl or $C_{3-7}$ cycloalkyl-$C_{1-3}$ alkyl, $R^2$ is $C_{1-6}$ alkoxy or hydrogen and $R^3$ is A-1.

In an eighth embodiment of the present invention there is provided a compound according to formula I wherein $R^1$ is CH=CHAr and $R^3$ is A-2.

In an ninth embodiment of the present invention there is provided a compound according to formula I wherein $R^1$ is CH=CHAr, Ar is phenyl substituted at the four-position by $NR^aR^b$ and optionally further substituted at one of the open positions, $R^a$ is hydrogen, $R^b$ is $SO_2R^6$ wherein $R^6$ is $C_{1-6}$ alkyl, $C_{3-7}$ cycloalkyl or $C_{3-7}$ cycloalkyl-$C_{1-3}$ alkyl and $R^2$ is $C_{1-6}$ alkoxy or hydrogen and $R^3$ is A-2.

In another embodiment of the present invention there is provided a compound according to formula I wherein $R^1$ is 2-naphthalene substituted at the 6-position by $NR^aR^b$ wherein $R^a$ is hydrogen, $R^b$ is $SO_2R^6$, $R^6$ is $C_{1-6}$ alkyl, $C_{3-7}$ cycloalkyl or $C_{3-7}$ cycloalkyl-$C_{1-3}$ alkyl, $R^2$ is $C_{1-6}$ alkoxy or hydrogen and $R^3$ is A-2.

In a tenth embodiment of the present invention there is provided a compound according to formula I wherein $R^1$ is CH=CHAr, $R^3$ is A-3 and $R^9$ is hydrogen.

In an eleventh embodiment of the present invention there is provided a compound according to formula I wherein $R^1$ is CH=CHAr, Ar is phenyl substituted at the four-position by $NR^aR^b$ and optionally further substituted at one of the open positions, $R^a$ is hydrogen, $R^b$ is $SO_2R^6$ wherein $R^6$ is $C_{1-6}$ alkyl, $C_{3-7}$ cycloalkyl or $C_{3-7}$ cycloalkyl-$C_{1-3}$ alkyl, $R^2$ is $C_{1-6}$ alkoxy or hydrogen and $R^3$ is A-3.

In another embodiment of the present invention there is provided a compound according to formula I $R^1$ is 2-naphthalene substituted at the 6-position by $NR^aR^b$ wherein $R^a$ is hydrogen, $R^b$ is $SO_2R^6$, $R^6$ is $C_{1-6}$ alkyl, $C_{3-7}$ cycloalkyl or $C_{3-7}$ cycloalkyl-$C_{1-3}$ alkyl, $R^2$ is $C_{1-6}$ alkoxy or hydrogen, $R^3$ is A-3 and $R^9$ is hydrogen.

In a twelfth embodiment of the present invention there is provided a compound according to formula I wherein $R^1$ is CH=CHAr and $R^3$ is A-4.

In a thirteenth embodiment of the present invention there is provided a compound according to formula I wherein $R^1$ is CH=CHAr, Ar is phenyl substituted at the four-position by $NR^aR^b$ and optionally further substituted at one of the open positions, $R^a$ is hydrogen, $R^b$ is $SO_2R^6$ wherein $R^6$ is $C_{1-6}$ alkyl, $C_{3-7}$ cycloalkyl or $C_{3-7}$ cycloalkyl-$C_{1-3}$ alkyl, $R^2$ is $C_{1-6}$ alkoxy or hydrogen and $R^3$ is A-4.

In another embodiment of the present invention there is provided a compound according to formula I wherein $R^1$ is 2-naphthalene substituted at the 6-position by $NR^aR^b$ wherein $R^a$ is hydrogen, $R^b$ is $SO_2R^6$, $R^6$ is $C_{1-6}$ alkyl, $C_{3-7}$ cycloalkyl or $C_{3-7}$ cycloalkyl-$C_{1-3}$ alkyl, $R^2$ is $C_{1-6}$ alkoxy or hydrogen, $R^3$ is A-4.

In a fourteenth embodiment of the present invention there is provided a compound according to formula I selected from compounds I-1 to I-4 in TABLE I.

In a fifteenth embodiment of the present invention there is provided a compound according to formula I selected from compounds II-1 to II-8 in TABLE II.

In a sixteenth embodiment of the present invention there is provide a method of treating a HCV infection in a patient in need thereof comprising administering a therapeutically effective amount of a compound according to formula I wherein $R^1, R^2, R^3, R^4, R^5, R^6, R^7, R^8, R^9, R^a, R^b, R^c, R^d, X^1, X^2$, Ar and m are as defined herein above.

In a seventeenth embodiment of the present invention there is provide a method of treating a HCV infection in a patient in need thereof comprising co-administering a therapeutically effective amount of a compound according to formula I wherein $R^1, R^2, R^3, R^4, R^5, R^6, R^7, R^8, R^9, R^a, R^b, R^c, R^d, X^1, X^2$, Ar and m are as defined herein above and at least one immune system modulator and/or at least one antiviral agent that inhibits replication of HCV.

In a eighteenth embodiment of the present invention there is provide a method of treating a disease caused by HCV in a patient in need thereof comprising co-administering a therapeutically effective amount of a compound according to formula I wherein $R^1, R^2, R^3, R^4, R^5, R^6, R^7, R^8, R^9, R^a, R^b, R^c, R^d, X^1, X^2$, Ar and m are as defined herein above and at least one immune system modulator selected from interferon, interleukin, tumor necrosis factor or colony stimulating factor.

In a nineteenth embodiment of the present invention there is provide a method of treating a HCV infection in a patient in need thereof comprising co-administering a therapeutically effective amount of a compound according to formula I wherein $R^1, R^2, R^3, R^4, R^5, R^6, R^7, R^8, R^9, R^a, R^b, R^c, R^d, X^1, X^2$, Ar and m are as defined herein above and an interferon or chemically derivatized interferon.

In a twentieth embodiment of the present invention there is provide a method of treating a HCV infection in a patient in need thereof comprising co-administering a therapeutically effective amount of a compound according to formula I wherein $R^1, R^2, R^3, R^4, R^5, R^6, R^7, R^8, R^9, R^a, R^b, R^c, R^d, X^1, X^2$, Ar and m are as defined herein above and another antiviral compound selected from the group consisting of a HCV protease inhibitor, another HCV polymerase inhibitor, a HCV helicase inhibitor, a HCV primase inhibitor and a HCV fusion inhibitor.

In a twenty-first embodiment of the present invention there is provided a method for inhibiting viral replication in a cell by delivering a therapeutically effective amount of a compound of the formula I wherein $R^1$, $R^2$, $R^3$, $R^4$, $R^5$, $R^6$, $R^7$, $R^8$, $R^9$, $R^a$, $R^b$, $R^c$, $R^d$, $X^1$, $X^2$, Ar and m are as defined herein above admixed with at least one pharmaceutically acceptable carrier, diluent or excipient.

In a twenty-second embodiment of the present invention there is provided a composition comprising a compound according to formula I wherein $R^1$, $R^2$, $R^3$, $R^4$, $R^5$, $R^6$, $R^7$, $R^8$, $R^9$, $R^a$, $R^b$, $R^c$, $R^d$, $X^1$, $X^2$, Ar and m are as defined herein above with at least one pharmaceutically acceptable carrier, diluent or excipient.

The term "alkyl" as used herein without further limitation alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, lower alkyl groups include methyl, ethyl, propyl, iso-propyl, n-butyl, tert-butyl, tert-butyl, neopentyl, hexyl, and octyl. Any carbon hydrogen bond can be replaced by a carbon deuterium bond with departing from the scope of the invention.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (hetero)aryl refers to either an aryl or a heteroaryl group.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —CH$_2$CH(i-Pr)CH$_2$—), unless otherwise indicated. $C_{0-4}$ alkylene refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkylalkyl" as used herein refers to the radical R'R"-, wherein R' is a cycloalkyl radical as defined herein, and R" is an alkylene radical as defined herein] with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cyclolalkyl and R" is $C_{1-3}$ alkylene as defined herein.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 12-fluoroethyl, 2-chloroethyl, 2-bromoethyl, 2,2-dichloroethyl, 3-bromopropyl or 2,2,2-trifluoroethyl. The term "fluoroalkyl" as used herein refers to a haloalkyl moiety wherein fluorine is the halogen.

The term "halogen" or "halo" as used herein means fluorine, chlorine, bromine, or iodine.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The terms "alkoxycarbonyl" and "aryloxycarbonyl" as used herein denotes a group of formula —C(=O)OR wherein R is alkyl or aryl respectively and alkyl and aryl are as defined herein.

The term "carbamoyl" as used herein means the radical —CONH$_2$. The prefix "N-alkylcabamoyl" and "N,N-dialkylcarbamoyl" means a radical CONHR' or CONR'R" respectively wherein the R' and R" groups are independently alkyl as defined herein. The prefix N-arylcarbamoyl" denotes the radical CONHR' wherein R' is an aryl radical as defined herein.

The terms "alkylsulfonylamido" and "arylsulfonylamido" as used herein denotes a group of formula —NR'S(=O)$_2$R wherein R is alkyl or aryl respectively, R' is hydrogen or $C_{1-3}$ alkyl, and alkyl and aryl are as defined herein.

The term "acyl" (or "alkanoyl") as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl or "alkanoyl" refers to a group —C(=O)R contain 1 to 6 carbon atoms. The $C_1$ acyl group is the formyl group wherein R=H and a C6 acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The term "cyclic amine" as used herein refers to a saturated carbon ring, containing from 3 to 6 carbon atoms as defined above, and wherein at least one of the carbon atoms is replaced by a heteroatom selected from the group consisting of N, O and S, for example, piperidine, piperazine, morpholine, thiomorpholine, di-oxo-thiomorpholine, pyrrolidine, pyrazoline, imidazolidine, azetidine wherein the cyclic carbon atoms are optionally substituted by one or more substituents, selected from the group consisting of halogen, hydroxy, phenyl, lower alkyl, lower alkoxy or 2-hydrogen atoms on a carbon are both replace by oxo (=O). When the cyclic amine is a piperazine, one nitrogen atom can be optionally substituted by $C_{1-6}$ alkyl, $C_{1-6}$ acyl, $C_{1-6}$ alkylsulfonyl.

Compounds of the present invention and their isomeric forms and pharmaceutically acceptable salts thereof are also useful in treating viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and anti-infective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759, GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Examples of the HCV NS3 protease inhibitors include, but are not limited to SCH-503034 (Schering, SCH-7), VX-950 (telaprevir, Vertex), BILN-2065 (Boehringer-Ingelheim, BMS-605339 (Bristol Myers Squibb), and ITMN-191 (Intermune).

Examples of the interferons include, but are not limited to pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen and actimmune, IFN-omega with DUROS, albuferon, locteron, Albuferon, Rebif, oral interferon alpha, IFNalpha-2b XL, AVI-005, PEG-Infergen, and pegylated IFN-beta.

Ribavirin analogs and the ribavirin prodrug viramidine (taribavirin) have been administered with interferons to control HCV.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexyl-carbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), ethyl (Et), ethanol (EtOH), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl acetate (EtOAc), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-$BuMe_2Si$ (TBDMS), triethylamine (TEA or $Et_3N$), triflate or $CF_3SO_2$— (TO, trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n-), iso (i-), secondary (sec-), tertiary (tent-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I

| Cmpd No. | Structure | IC$_{50}$ nM[1] | mp | MS [M + H]+ |
|---|---|---|---|---|
| I-1 | 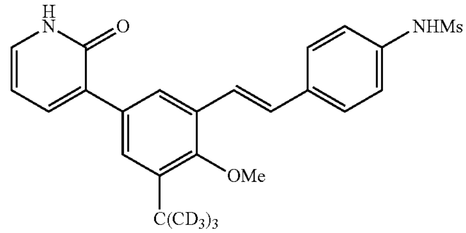 | 0.2 | | 476.3 |
| I-2 | 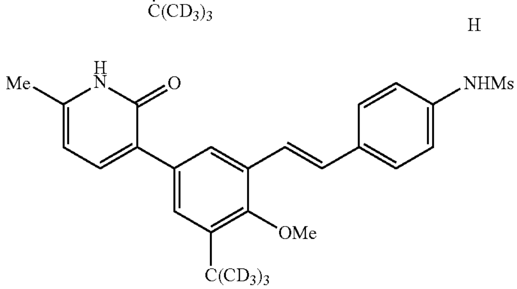 | <0.13 | H | 490.3 |
| I-3 | 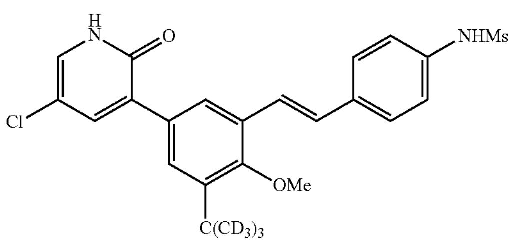 | 0.5 | | 510.2 |
| I-4 | 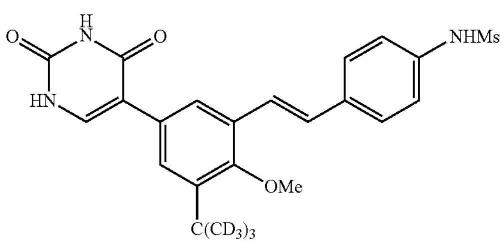 | | | 493.2 |

[1]HCV Polymerase Assay as described in Example 5

4-bromo-2-[1,1-di(methyl-d$_3$)ethyl-2,2,2-d$_3$]-phenol was prepared by introducing the (CD$_3$)$_3$C moiety via a Friedel-Crafts alkylation of A-1 (step 1) with 2-(methyl-d$_3$)-2-propan-1,1,1,3,3,3-d$_6$-ol-d (CASRN 53001-22-2) after exchanging the labile OH proton with deuterium. The resulting phenol is carbonylated (step 2) with paraformaldehyde and O-methylated (step 3) with iodomethane to afford A-3. One skilled in the art will appreciate that bromination of A-2a will afford 4,6-dibromo-2-[1,1-di(methyl-d$_3$)ethyl-2,2,2-d$_3$]-phenol which can also be O-methylation and subsequently serve as a useful synthetic intermediate susceptible to successive palladium-catalyzed couplings at the brominated carbons to afford compounds within the scope of the present invention. (see, e.g., U.S. Ser. No. 12/460,658 filed Jul. 22, 2009 which is hereby incorporated by reference in its entirety).

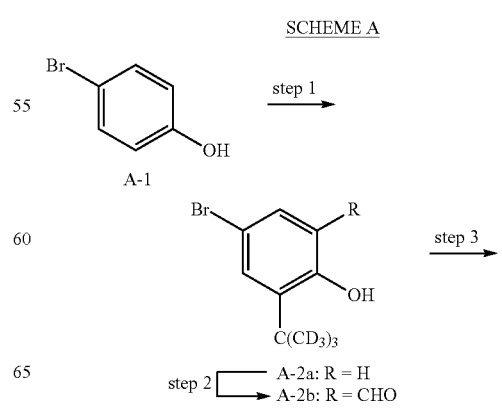

SCHEME A

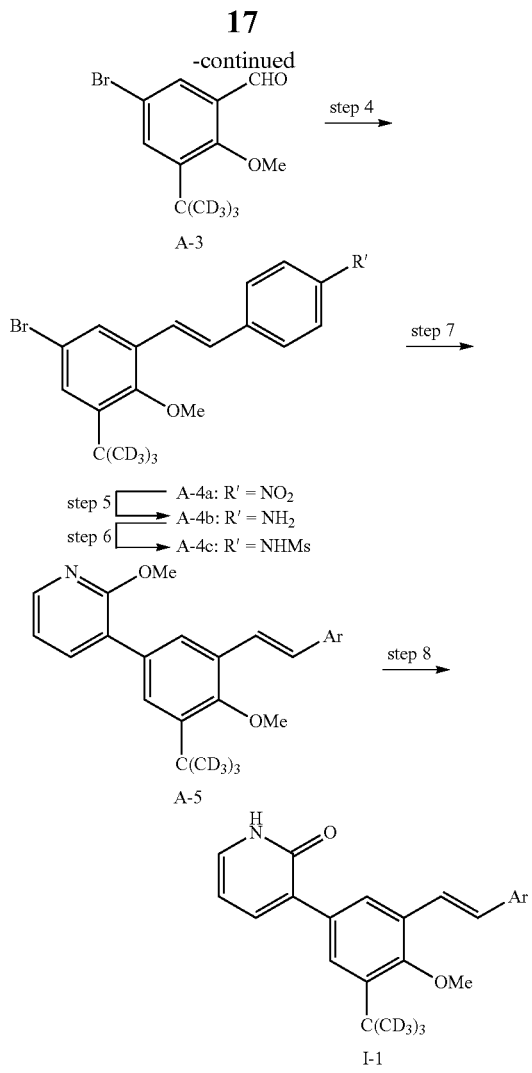

Ar = 4-methansulfonamido-phenyl

3-[3-tert-Butyl-4-methoxy-5-((E)-styryl)-phenyl]-1H-pyridin-2-one derivatives (e.g. D-8) are prepared from A-3 utilizing a Wittig homologation with benzyl-triphenyl-$X^5$-phosphane or the conjugate base of a diethylbenzylphosphonate or a substituted analog thereof (step 4).

The Wittig reaction is the reaction of an aldehyde or ketone with a triphenyl phosphonium ylide to afford an alkene and triphenylphosphine oxide. (A. Maercker, *Org. React.* 1965, 14, 270-490; A. W. Carruthers, Some Modern Methods of Organic Synthesis, Cambridge University Press, Cambridge, UK, 1971, pp 81-90) Wittig reactions are most commonly used to condense aldehydes or ketones to singly substituted phosphine ylides. The Wittig reagent is usually prepared from a phosphonium salt, which is, in turn, prepared by alkylation of $Ph_3P$ with an alkyl halide. To form the Wittig reagent (ylide), the phosphonium salt is suspended in a solvent such as $Et_2O$ or THF and a strong base such as phenyl lithium or n-butyllithium is added. With simple ylides, the product is usually mainly the Z-isomer, although a lesser amount of the E-isomer also is often formed. This is particularly true when ketones are used. If the reaction is performed in DMF in the presence of LiI or NaI, the product is almost exclusively the Z-isomer. If the E-isomer is the desired product, the Schlosser modification may be used. Alternatively the Horner-Wadsworth-Emmons reaction (B. E. Maryanoff and A. B. Reitz, *Chem. Rev.* 1989 89:863-927) produces predominantly E-alkenes. The Horner-Wadsworth-Emmons reaction (HWE reaction) is the condensation of stabilized phosphonate carbanions with aldehydes (or ketones). The requisite dialkyl phosphonates are prepared by reacting a benzyl halide and a trialkylphosphite. In contrast to phosphonium ylides used in the Wittig reaction, phosphonate-stabilized carbanions are more nucleophilic and more basic.

Compounds encompassed by the present invention wherein $R^1$ is an optionally substituted amino-phenylethyl moiety can be prepared from a nitrobenzyl phosphonate. Thus condensation of A-3 and diethyl (4-nitro-benzyl)-phosphonate and subsequent reduction of the nitro substituent (step 5) affords the amine A-4-b. Suitable reducing agents include, e.g., $LiAlH_4$, $LiBH_4$, Fe, Sn or Zn, in a reaction inert solvent, e.g. MeOH, EtOH, diglyme, benzene, toluene, xylene, o-dichlorobenzene, DCM, DCE, THF, dioxane, or mixtures thereof. If desired, when the reducing reagent is Fe, Sn or Zn, the reaction is carried out under acidic conditions in the presence of water. Catalytic hydrogen allows concomitant reduction of the styrene and the nitro substituent. Alternatively, an optionally substituted benzyl-triphenyl-$X^5$-phosphane can be condensed with A-3 and similarly converted to an optionally substituted phenylethyl moiety. Sulfonylation or acylation of the resulting amine, if desired, is carried out by treating the amine with an activated carboxylic acid or a sulfonyl halide, typically in the presence of an tertiary amine base to remove HCl liberated during the reaction.

The 1H-pyridin-2-one moiety was introduced by palladium-catalyzed Suzuki coupling of a 2-alkoxy-pyridin-3-yl boronic, 2-benzyloxy-pyridin-3-yl boronic acid or boronic acid ester and the aryl bromide A-4-c (step 7). Subsequent cleavage of the ether bond (step 8) affords the desired pyridone. 2-Alkoxy-pyridin-3-yl boronic acids without additional substitution on the pyridine ring also are available. One skilled in the art will appreciate coupling protocols exist which can be adopted when advantageous. For example, the coupling can be carried out with, B-(1,2-dihydro-2-oxo-3-pyridinyl) boronic acid (CASRN 951655-49-5). In addition the coupling can also be accomplished by introducing a boronic acid or equivalent thereof into A-4-c and carrying out the coupling with a halo substituted heteroaryl compound. The optimal route frequently is determined by the availability of the requisite starting materials.

The Suzuki reaction is a palladium-catalyzed coupling of a boronic acid with an aryl or vinyl halide or triflate. Typical catalysts include $Pd(PPh_3)_4$, $PdCl_2(dppf)$, $Pd(OAc)_2$ and $PdCl_2(PPh_3)_2$. With $PdCl_2(dppf)$, primary alkyl borane compounds can be coupled to aryl or vinyl halide or triflate without beta-elimination. The reaction can be carried out in a variety of organic solvents including toluene, THF, dioxane, DCE, DMF, DMSO and MeCN, aqueous solvents and under biphasic conditions. Reactions are typically run from about RT to about 150° C. Additives (e.g., CsF, KF, T10H, NaOEt and KOH) frequently accelerate the coupling. Although there are numerous components in the Suzuki reaction such as the particular palladium catalyst, the ligand, additives, solvent, temperature, numerous protocols have been identified. Highly active catalysts have been described (see, e.g., J. P. Wolfe et al., *J. Am. Chem. Soc.* 1999 121(41):9550-9561 and A. F. Littke et al., *J. Am. Chem. Soc.* 2000 122(17):4020-4028). One skilled in the art will be able to identify a satisfactory protocol without undue experimentation.

Compounds wherein $R^1$ is an ((E)-styryl)-phenyl moiety also be prepared by condensation of substituted toluene derivatives with A-3. This is most practical when toluene is substituted with electronegative groups which increase the acidity of protons on the methyl group and allow formation of the anion which adds to the carbonyl and undergoes subsequent dehydration of the initially formed carbinol. (see e.g, referential example 1) The condensation in referential example 1 is carried out with methyl 2-methyl-5-nitro-benzoate. After conversion of the nitro moiety into a methanesulfonamide (supra), the methyl ester can be further modified by, e.g., hydrolysis to the corresponding acid, reduction to the benzyl alcohol (referential example 2) which optionally can be subsequently O-alkylated (referential example 3). Direct oxidation to the aldehyde or re-oxidation of the benzyl alcohol to the aldehyde affords an synthetic intermediate which can be used to homologate substituent or incorporate further functionality by, e.g., reductive alkylation to introduce an amine a Claisen or Aldol condensation of a carbanion with the aldehyde or a Wittig reaction.

Alternately, the phenylethyl side chain can be elaborated by converting A-3 to 5-bromo-1-tert-butyl-3-ethynyl-2-methoxy-benzene (step 2, referential example 4) The acetylene is prepared by condensing A-3 with (1-diazo-2-oxo-propyl)-phosphonic acid diethyl ester. (R. Muller et al. *Syn Lett* 1996 6:521). Hydrostannylation of the acetylene affords a trialkylvinylstannane derivative which can be subjected to palladium-catalyzed coupling with an aryl or heteroaryl halide such as 5-amino-2-iodo-pyridine or other appropriately substituted halo- or trifluorosulfonyloxy-aryl or heteroaryl derivative (i.e., a Sonogashira coupling). Numerous substituted aryl or heteroaryl iodides can be used advantageously (referential example 4). Reduction of the acetylene is carried out by conventional techniques and dealkylation of the pyridinyl ether affords the desired pyridone.

The Sonogashira coupling (K. Sonogashira et al., *Tetrahedron Lett.* 1975 4467-4470; K. Sonogashira, *Comprehensive Organic Synthesis*; B. M. Trost and I. Fleming Eds.; Pergamon Press, Oxford, 1991; Vol. 3, Chapter 2.4, p 521) is typically carried out in the presence of a palladium catalyst such as $Pd(PPh_3)_4$ or $Pd(II)Cl_2(PPh_3)_2$ and a cuprous salt, for example CuI, a dialkyl- or trialkylamine such as diethylamine, diisopropylamine, TEA and the like at temperature from RT to 100° C. The reaction can be carried out using the amine base as the solvent or with other organic solvents including hydrocarbons, ethers, alcohols, aqueous DMA and the like. The existence of alternative procedures affords flexibility in the synthetic planning permitting introduction of a variety of substituted aryl and heteroaryl substituents.

Another alternative approach is to brominate A-2a to afford 2,4-dibromo-6-tert-butyl-phenol (F—N. Li et al., *Bioorg. Med. Chem.* 2009 17:3557) and subsequently O-alkylate the phenol to afford 1,5-dibromo-3-tent-butyl-2-methoxy-benzene which can be subjected to sequential palladium-catalyzed couplings to afford compounds within the scope of the present invention.

Prodrugs of compounds according to formula I wherein $R^3$ is A-1 can be prepared by treating the corresponding pyridone wherein $R^8$ is hydrogen with paraformaldehyde and acylating the resulting hydroxymethyl adduct. Phosphate prodrugs can be prepared by converting the hydroxymethyl adduct to a chloromethyl adduct and displacing the chlorine with a O-alkylating a phosphate. Representative procedures for formation of the prodrugs can be found in U.S. Patent Publication 2009/0170856 which is hereby incorporated by reference in its entirety.

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 8. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972. The cell-based replicon assay conditions used for compounds of the present invention are described in Example 4. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system. Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

N-(4-{(E)-2-[3-[1,1-di(methyl-$d_3$)ethyl-2,2,2-$d_3$]-2-methoxy-5-(2-oxo-1,2-dihydro-pyridin-3-yl)-phenyl]-vinyl}-phenyl)-methanesulfonamide (I-1) (SCHEME A)

step 1—A solution of $CD_3OD$ (25 mL) and A-1 (8.5 g, 49.2 mmol) is stirred at RT for 30 min to exchange the phenolic proton, and then $CD_3OD$ is removed in vacuo. The resulting solid is dissolved in $CDCl_3$ (10 mL) and $(CD_3)_3COD$ (4 mL) and warmed to 60° C. Concentrated $D_2SO_4$ (10 mL) is added in five 2 mL portions over 50 min. The reaction mixture is maintained at 60° C. overnight and then poured over ice (50 mL) and extracted with EtOAc (2×75 mL). The combined organic extracts are extracted with 2N aq. KOH (3×300 mL), washed with 1N aqueous HCl (75 mL) and brine (25 mL), dried ($MgSO_4$) and concentrated in vacuo. The residue is purified by $SiO_2$ chromatography eluting with an EtOAc/hexane gradient (0 to 10% EtOAc over 40 min) to afford 5.83 g of A-2a as a brown oil: ES MS (M+H) 238.1.

step 2—To a vigorously stirred suspension of the A-2a (5.8 g, 24.4 mmol), anhydrous $MgCl_2$ (4.6 g, 48.8 mmol) and paraformaldehyde (1.6 g, 53.7 mmol) in anhydrous THF (40 mL) at RT was added dropwise TEA (6.8 mL, 48.8 mmol). The reaction was heated at reflux overnight. The reaction was cooled to RT and the volatile components are removed in vacuo. The residue is dissolved in EtOAc (50 mL), washed with 1N aqueous HCl (2×50 mL) and brine (25 mL), dried ($MgSO_4$), filtered and concentrated in vacuo to afford 6.52 g of A-2b as a light brown oil which was used without further purification: ES MS (M+H) 266.1.

step 3—Iodomethane (3.8 g, 26.8 mmol) was added dropwise to a vigorously stirred suspension of the A-2b (6.5 g, 24.4 mmol) and $Cs_2CO_3$ (11.9 g, 36.6 mmol) in DMF (40 mL) at RT. The reaction was maintained at to 60° C. overnight. The reaction was cooled to RT and partitioned between $H_2O$ (150 mL) and EtOAc:PhMe (1:1, 100 mL). The phase was dried ($MgSO_4$), filtered and concentrated in vacuo to afford 6.5 g of A-3 as a light orange oil which was used without further purification: ES MS (M+H) 280.1.

step 4—A dark red suspension of NaH (1.10 g, 27.6 mmol, 60% mineral oil dispersion in oil) and 15-crown-5 (0.51 g, 2.3 mmol) in THF (80 mL) was stirred vigorously at RT for 5 min. The reaction is cooled to 0° C. and (4-amino-benzyl)-phosphonic acid diethyl ester was added. The reaction is maintained at 0° C. for 15 min. A solution of A-3 (6.45 g, 22.9 mmol) in THF (20 mL) was added dropwise, and the reaction maintained at 0° C. for 10 min. The mixture was warmed to RT and stirred for 16 h. The THF was removed in vacuo. The residue was dissolved in EtOAc (75 mL), washed with water (50 mL), dried ($MgSO_4$) and concentrated in vacuo to afford a yellow foam. The crude product was further purified by $SiO_2$ gel chromatography eluting with an EtOAc/hexane gradient (0 to 25% EtOAc over 30 min) to afford 6.1 g of A-4-a as a light yellow amorphous solid: ES MS (M+H) 399.1.

step 5—A vigorously stirred suspension of the A-4-a (5.8 g, 14.6 mmol), Fe powder (6 g), $NH_4Cl$ (6 g), EtOH (60 mL) and water (30 mL) was maintained at 70° C. for 16 h. The reaction mixture was filtered through CELITE® (washing with excess EtOH), and the EtOH was removed in vacuo. The resulting aqueous suspension was extracted with EtOAc (3×75 mL). The combined organic extracts were dried ($MgSO_4$), filtered and concentrated in vacuo to afford 5.23 g of A-4-b as a light brown solid which was used without further purification: ES MS (M+H) 370.2.

step 6—Methanesulfonyl chloride (1.68 g, 14.6 mmol) was added dropwise to a solution of the A-4-b (4.9 g, 13.3 mmol) in pyridine (20 mL) and DCM (20 mL) and the solution was maintained at RT for 18 h. The solvents were removed in vacuo. The resulting light brown residue was dissolved in EtOAc (75 mL) and washed sequentially with 1 N aq. HCl (75 mL) and brine (25 mL). The EtOAc extract was dried, filtered and concentrated in vacuo. The crude product was purified by $SiO_2$ chromatography eluting with an EtOAc/hexane gradient (0 to 40% EtOAc over 30 min) to afford 4.3 g of A-4-c as a white foam: ES MS (M+H) 462.2.

step 7—A mixture of the A-4-c (192 mg, 0.43 mmol), 2-methoxypyridine-3-boronic acid (21, 66 mg, 0.43 mmol), $Pd(PPh_3)_4$ (50 mg, 0.043 mmol), $Na_2CO_3$ (136 mg, 1.29 mmol), DCM (1 mL) and MeOH (3 mL) was combined in a 5 mL microwave vessel fitted with a teflon cap. The mixture was irradiated in a microwave synthesizer at 125° C. for 1.0 h. The mixture was filtered through CELITE and the pad washed with excess MeOH. The filtrate was concentrated and absorbed onto $SiO_2$ and purified by $SiO_2$ gel chromatography eluting with an EtOAc/hexane gradient (0-40% EtOAc over 30 min) to afford 0.165 g of A-5 as a white amorphous solid: ES MS (M+H) 490.3.

step 8—A solution of the A-5 (125 mg), 48% aqueous HBr (150 μL), and HOAc (2.6 mL) was maintained at 60° C. for 16 h in a sealed tube fitted with a Teflon cap. The reaction was cooled to RT, and cold water (20 mL) was added. A fine precipitate formed immediately. The precipitate was filtered filtration, washed with excess water, and dried overnight in a vacuum oven to afford 0.091 g of I-1 as an off-white powder (91 mg): ES MS (M+H) 476.3.

Example 2

N-(4-{(E)-2-[3-[1,1-di(methyl-d₃)ethyl-2,2,2-d₃]-2-methoxy-5-(2-oxo-6-methyl-1,2-dihydro-pyridin-3-yl)-phenyl]-vinyl}-phenyl)-methanesulfonamide (I-2)

I-2 was prepared in accord with example 1 except in step 7,2-methoxypyridine-3-boronic acid was replaced with (6-methyl-2-methoxypyridin-3-yl)boronic acid (CASRN 1000802-75-4): ES MS (M+H) 490.3.

Example 3

N-(4-{(E)-2-[3-[1,1-di(methyl-d₃)ethyl-2,2,2-d₃]-2-methoxy-5-(2-oxo-5-chloro-1,2-dihydro-pyridin-3-yl)-phenyl]-vinyl}-phenyl)-methanesulfonamide (I-3)

I-3 was prepared in accord with example 1 except in step 7,2-methoxypyridine-3-boronic acid was replaced with (5-chloro-2-methoxypyridin-3-yl)boronic acid (CASRN 943153-22-8): ES MS (M+H) 510.2.

Example 4

N-(4-{(E)-2-[3-[1,1-di(methyl-d₃)ethyl-2,2,2-d₃]-5-(2,4-dioxo-1,2,3,4-tetrahydro-pyrimidin-5-yl)-2-methoxy-phenyl]-vinyl}-phenyl)-methanesulfonamide (I-4)

I-4 was prepared in accord with example 1 except in step 7,2-methoxypyridine-3-boronic acid was replaced with (2,4-dioxo-1,2,3,4-tetrahydropyrimidin-5-yl)boronic acid (CASRN 70523-22-7) and step 8 was omitted: ES MS (M+H) 493.2.

N-(4-{(E)-2-[3-tert-Butyl-2-methoxy-5-(1-methyl-2,4-dioxo-1,2,3,4-tetrahydro-pyrimidin-5-yl)-phenyl]-vinyl}-phenyl)-methanesulfonamide can be prepared analogously except (2,4-dioxo-1,2,3,4-tetrahydropyrimidin-5-yl)boronic acid is replaced by (1,2,3,4-tetrahydro-1-methyl-2,4-dioxo-5-pyrimidinyl)-boronic acid.

The compounds in TABLE II are illustrative of other compounds within the scope of the present invention. The non-deuterated derivatives were disclosed in U.S. Ser. No. 12/460,658 filed Jul. 22, 2009 and U.S. Ser. No. 61/156,442 filed Feb. 27, 2009 and 61/139,982 filed Dec. 22, 2008 and the HCV polymerase data reported in TABLE II was measured with the non-deuterated analogs. One skilled in the art will appreciate that the isotopic composition of the tert-butyl group is not expected to significantly influence HCV polymerase inhibition. (For example, the $IC_{50}$ for compound the deuterated and (non-deuterated) analogs of I-1 to I-3 are 0.2 nM (3.9 nM), <0.13 nM (<0.7 nM) and 0.5 nM (1.0 nM), respectively.)

TABLE II

| Cmpd No. | Structure | $IC_{50}$ nM[1] |
|---|---|---|
| II-1 | 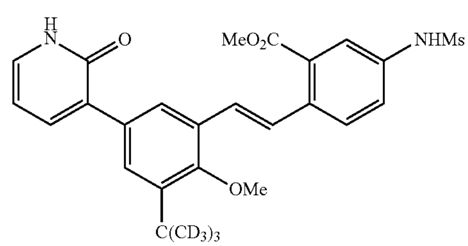 | 0.004 |
| II-2 | 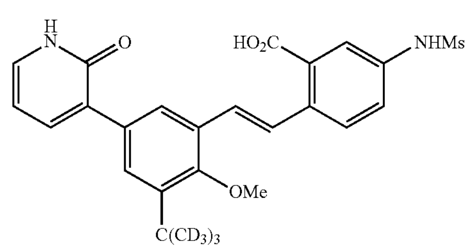 | 0.008[1] |
| II-3 | 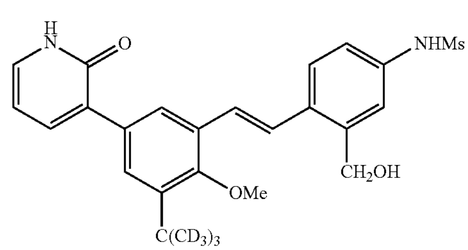 | 0.002[1] |

TABLE II-continued

| Cmpd No. | Structure | IC$_{50}$ nM[1] |
|---|---|---|
| II-4 | 3-(pyridin-2(1H)-one)-5-[(E)-2-(4-NHMs-2-CH$_2$OMe-phenyl)vinyl]-4-OMe-3-C(CD$_3$)$_3$-phenyl | 0.002[1] |
| II-5 | 5-Cl-3-(pyridin-2(1H)-one)-phenyl-[(E)-vinyl]-(5-NHMs-pyridin-2-yl), 4-OMe, 3-C(CD$_3$)$_3$ | 0.003[1] |
| II-6 | 3-(pyridin-2(1H)-one)-phenyl-[(E)-vinyl]-(6-NHMs-pyridin-3-yl), 4-OMe, 3-C(CD$_3$)$_3$ | 0.003[1] |
| II-7 | 5-F-3-(pyridin-2(1H)-one)-phenyl-[(E)-vinyl]-(4-NHMs-2-F-phenyl), 4-OMe, 3-C(CD$_3$)$_3$ | 0.001[1] |
| II-8 | 5-(1,2,4-triazin-6(1H)-one)-phenyl-[(E)-vinyl]-(4-NHMs-phenyl), 4-OMe, 3-C(CD$_3$)$_3$ | 0.0004[1] |

* IC$_{50}$ observed with the corresponding non-deuterated analog

The following procedures illustrate the synthesis of non-deuterated analogs of compounds from TABLE II using 5-bromo-3-tent-butyl-2-hydroxy-benzaldehyde (cf., A-3) as an intermediate. One skilled in the art will immediately appreciate that similar procedures can be used to prepare the deuterated compounds in Table II.

Referential Example 1

2-{(E)-2-[3-tert-Butyl-2-methoxy-5-(2-oxo-1,2-dihydro-pyridin-3-yl)-phenyl]-vinyl}-5-methanesulfonylamino-benzoic acid methyl ester (26a)

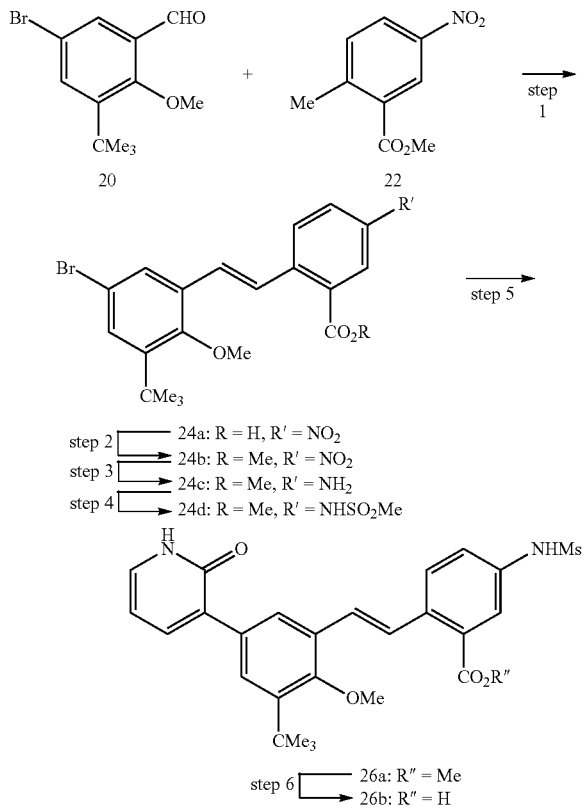

step 1—A solution of 20 (4.17 g, 15.39 mmol), 22 (2.00 g, 10.26 mmol), DBU (3.1 mL, 20.73 mmol) and DMSO (10 mL) was stirred overnight at RT then heated to 50° C. for 1 h. To the solution was added 1N NaOH and the resulting solid filtered. The filtrate was acidified with 6N HCl extracted with EtOAc and the combined extracts dried ($Na_2SO_4$), filtered and evaporated to afford 2.51 g of 24a.

step 2—A solution of 24a (2.00 g, 4.608 mmol) iodomethane (1.05 mL, 16.87 mmol), $K_2CO_3$ (1.92 g, 13.89 mmol) and DMF (10 mL) was stirred overnight at RT. The resulting solution was filtered and the filtrate was diluted with EtOAc and washed with 1N HCl, $H_2O$ and brine. The organic phase was dried ($Na_2SO_4$), filtered and concentrated in vacuo to afford 1.94 g (94%) of 24b.

step 3—To a solution of 24b (1.42 g, 3.18 mmol) in DMF (10 mL) and EtOAc (10 mL) was added $SnCl_2$ (2.87 g, 12.72 mmol) and the resulting solution stirred at RT overnight. The reaction mixture was cooled to 0° C. and quenched by slow addition of aq. $NaHCO_3$ (4 mL). The resulting suspension was filtered through a pad of CELITE and the filtrate diluted with EtOAc, thrice washed with brine, dried ($Na_2SO_4$), filtered and concentrated in vacuo. The crude product was purified by $SiO_2$ chromatography eluting with a EtOAc/hexane gradient (10 to 20% EtOAc) to afford 843 mg (64%) of 24c as a yellow foam.

step 4—The methanesulfonamide was prepared by treatment of 24c with mesyl chloride in accord with the procedure in step 3 of example 6. The crude product was purified by $SiO_2$ chromatography eluting with a EtOAc/hexane gradient (10 to 30% EtOAc) to afford 697 mg (704%) of 24d.

step 5—The palladium-catalyzed coupling of 24d and B-(1,2-dihydro-2-oxo-1,2-dihydro-pyridin-3-yl) boronic acid (25, CASRN 951655-49-5) was carried out in accord with the procedure in step 7 of example 1 to afford the title compound. The product was purified on a $SiO_2$ preparative TLC plate developed with EtOAc/hexane (2:1) to afford 19.4 mg of 26a.

26b can be prepared by base-catalyzed hydrolysis of 26a with lithium hydroxide in an aqueous MeOH/THF at RT.

Referential Example 2

N-(4-{(E)-2-[3-tert-Butyl-2-methoxy-5-(2-oxo-1,2-dihydro-pyridin-3-yl)-phenyl]-vinyl}-3-hydroxymethyl-phenyl)-methanesulfonamide (28)

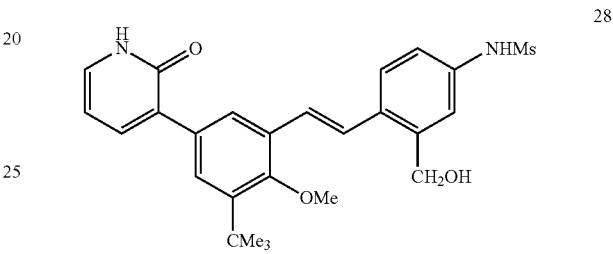

step 1—To a solution of 24d (184 mg, 0.371 mmol) in THF (10 mL) at 0° C., was added $LiAlH_4$ (0.750 mL, 0.750 mmol, 1.0 M solution in THF). The reaction was gradually warmed to RT over 1.5 hr, then cooled down to 0° C. and quenched with 1N NaOH (2 mL). The suspension was extracted with EtOAc and the combined extracts dried ($Na_2SO_4$), filtered and concentrated in vacuo. The crude product was purified by $SiO_2$ chromatography eluting with an EtOAc/hexane gradient (30% to 50% EtOAc) to afford 73 mg (42%) of N-{4-[(E)-2-(5-bromo-3-tert-butyl-2-methoxy-phenyl)-vinyl]-3-hydroxymethyl-phenyl}-methanesulfonamide (30).

Cross coupling of the 30 and 25 was carried out in accord with the procedure in step 7 of example 1. The crude product was purified on a $SiO_2$ preparative TLC plate developed with 2:1 EtOAc/hexane and further purified by HPLC to afford 15 mg (20%) of 28 as a white solid.

Referential Example 3

N-(4-{(E)-2-[3-tert-Butyl-2-methoxy-5-(6-methyl-2-oxo-1,2-dihydro-pyridin-3-yl)-phenyl]-vinyl}-3-methoxymethyl-phenyl)-methanesulfonamide (38)

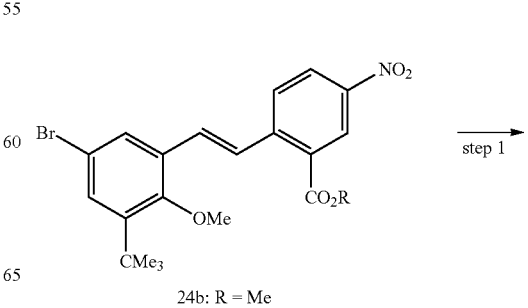

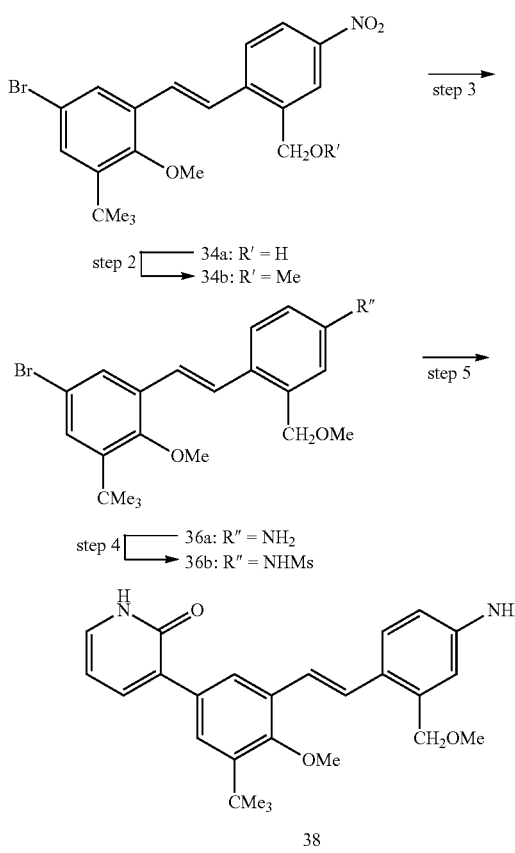

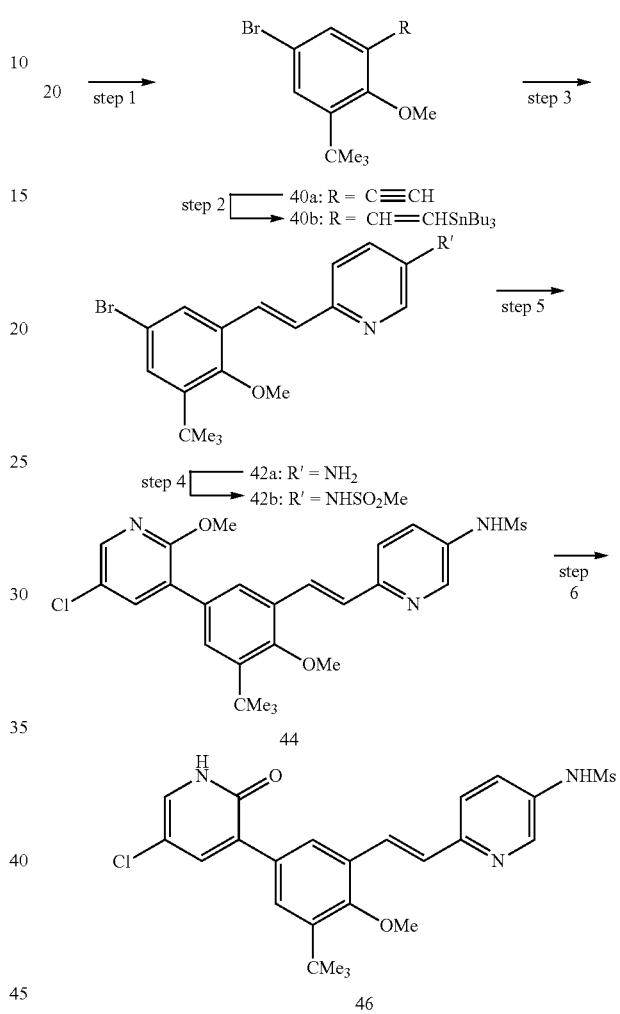

Referential Example 4

N-(6-{(E)-2-[3-tert-Butyl-5-(5-chloro-2-oxo-1,2-dihydro-pyridin-3-yl)-2-methoxy-phenyl]-vinyl}-pyridin-3-yl)-methanesulfonamide (46)

step 1—To a solution of 24b (500 mg, 1.12 mmol) in THF (10 mL) cooled to 0° C., was added LiAlH₄ (1.7 mL, 1.7 mmol, 1.0 M solution in THF). The reaction was gradually warmed to RT over 45 min, then re-cooled down to 0° C. and quenched with NaHSO₄ solution. The suspension was concentrated, diluted with EtOAc, and washed with 1N HCl and brine. The organic extract was dried (Na₂SO₄), filtered and concentrated in vacuo. The crude product was purified by SiO₂ chromatography eluting with an EtOAc/hexane gradient (5% to 10% EtOAc) to afford 129 mg (28%) of {2-[(E)-2-(5-bromo-3-tert-butyl-2-methoxy-phenyl)-vinyl]-5-nitro-phenyl}-methanol (34a) as a yellow oil.

step 2—To a solution of 34a (116 mg, 0.276 mmol) in DMF (5 mL) was added sodium hydride (0.022, 0.550 mmol, 60% mineral oil dispersion). After 20 min, methyl iodide (0.040 mL, 0.643 mmol) was added and the resulting suspension was stirred overnight. The reaction mixture was diluted with EtOAc, thrice washed with brine, dried (Na₂SO₄), filtered and concentrated in vacuo. The crude product was purified by SiO₂ chromatography eluting with an EtOAc/hexane gradient (5% to 15% EtOAc) to afford 81 mg (68%) of 5-bromo-1-tert-butyl-2-methoxy-3-[(E)-2-(2-methoxymethyl-4-nitro-phenyl)-vinyl]-benzene (34b) as an orange oil.

Reduction of the nitro group (step 3) is carried out with SnCl₂·2H₂O in DMF and EtOAc. Sulfonylation of 36a to afford 36b was carried out in accord with the procedure described in step 6 of Example 1. Cross coupling of the bromide and 25 is carried out in accord with the procedure in step 7 of example 1.

step 1—To a solution of 20 (2.667 mmol) in MeOH (20 mL) cooled to −78° C., is added a solution of sodium methoxide (0.5M in MeOH, 5.500 mmol) followed by dropwise addition of a solution of dimethyl 1-diazo-2-oxopropylphosphonate (4.000 mmol) in MeOH (10 mL). The resulting reaction mixture is gradually warmed to RT and is stirred overnight then quenched with a saturated aqueous NaHCO₃. The organic volatiles are removed under reduced pressure. The crude residue is partitioned between EtOAc and saturated aqueous NaHCO₃. The organic layer is washed with water, brine, and dried (Na₂SO₄), filtered and concentrated. The crude residue is purified by SiO₂ chromatography eluting with an EtOAc/hexane gradient to afford 40a.

step 2—To a solution of 40a (0.390 g, 1.32 mmol) dissolved in THF (4 mL) and benzene (4 mL) maintained under an Ar atmosphere at RT is added AIBN (0.53 mmol) followed by dropwise addition of Bu₃SnH (0.528 mmol). The reaction mixture is heated at 90° C. for 2 h, cooled to RT and concentrated in vacuo. The crude product is purified by SiO₂ chromatography eluting with EtOAc/hexane to afford 40b.

step 3—A solution of Pd$_2$(dba)$_3$ (0.027 mmol), tris-(2-furyl)phosphine (0.107 mmol) in DMF (2.0 mL) is stirred for 10 min at RT. To this solution is added via cannula a solution of 40b (1.33 mmol), 5-amino-2-iodo-pyridine (1.6 mmol, CASRN 29958-12-1) and DMF (6 mL). To the resulting solution at RT is added LiCl (2.67 mmol) and the resulting solution is heated at 110° C. for 18 h. The reaction is cooled to RT, poured into H$_2$O (80 mL) and the solution thrice extracted with EtOAc. The combined extracts are washed sequentially with H$_2$O and brine, dried, filtered and evaporated. The crude product is purified by SiO$_2$ chromatography eluting with a EtOAc/hexane gradient to afford 42a.

Conversion of the amino group to the sulfonamide 42b with mesyl chloride (step 4) was carried out in accord with the procedures described in step 6 of example 1. Cross coupling of 42b and 5-chloro-2-methoxy-pyridin-3-yl boronic acid is carried out in accord with the procedure in step 7 of example 1. Cleavage of the pyrindinyl methyl ether was accomplished with HBr/HOAc in accord with the procedure described in step 8 of example 1 to afford 46.

N-(5-{(E)-2-[3-tert-Butyl-2-methoxy-5-(2-oxo-1,2-dihydro-pyridin-3-yl)-phenyl]-vinyl}-pyridin-2-yl)-methanesulfonamide was prepared analogously except in step 3,5-amino-2-iodo-pyridine was replaced with 2-amino-5-iodo-pyridine (CASRN 20511-12-0) and in step 5,5-chloro-2-methoxy-pyridin-3-yl boronic acid is replaced with 21.

N-(4-{(E)-2-[3-tert-Butyl-5-(5-fluoro-2-oxo-1,2-dihydro-pyridin-3-yl)-2-methoxy-phenyl]-vinyl}-3-fluoro-phenyl)-methanesulfonamide was prepared analogously except in step 3,5-amino-2-iodo-pyridine was replaced with N-(4-bromo-3-fluoro-phenyl)-methanesulfonamide (CASRN 879486-59-6) and in step 5,5-chloro-2-methoxy-pyridin-3-yl boronic acid is replaced with 5-fluoro-2-methoxy-pyridin-3-yl boronic acid 1: MS (WSI) (M+H)=489.

Referential Example 5

N-(4-{(E)-2-[3-tert-Butyl-2-methoxy-5-(6-oxo-1,6-dihydro-[1,2,4]triazin-5-yl)-phenyl]-vinyl}-phenyl)-methanesulfonamide (62)

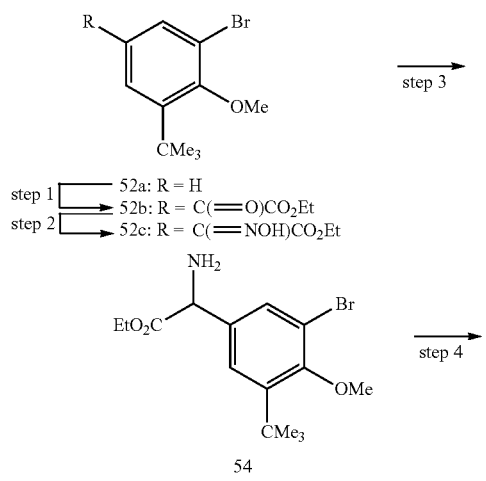

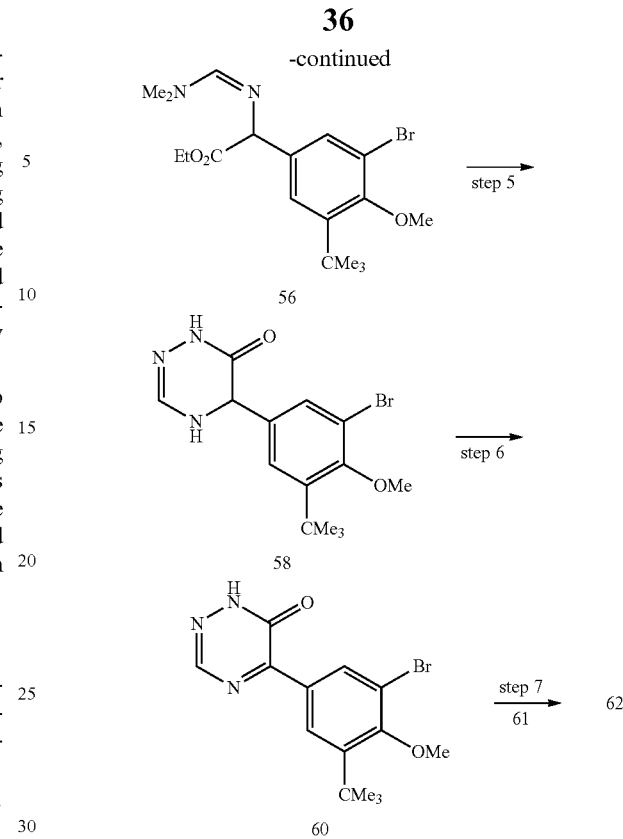

step 1—To a suspension of AlCl$_3$ (4.19 g, 31 mmol) and DCM (25 mL) cooled to 0° C. and maintained under nitrogen was added was added dropwise over 10 min ethyl chloroformate (4.24 g, 31 mmol) and the resulting solution was stirred for an additional 15 min. To the resulting solution was added dropwise over 15 min via syringe 52a (4.0 g, 16 5 mmol, which can be prepared by NBS bromination of A-2a and subsequent O-methylation as described in Example 1 supra). The resulting solution was allowed to warm to RT and stirring was continued for 1.5 h. The solution was poured into a mixture of ice (150 g) and con HCl (50 mL) and the resulting mixture extracted with DCM (3×50 mL). The combined organic extracts were washed with dilute NaOH, then twice with brine, dried (Na$_2$SO$_4$), filtered and concentrated in vacuo. The crude product was purified by SiO$_2$ chromatography eluting with 10% EtOAc/hexane to afford 4.22 g (74%) of 52b step 2—A solution of 52b (4.2 g, 12.2 mmol), hydroxylamine hydrochloride (1.36 g, 19.6 mmol), NaOAc (1.1 g, 14 5 mmol) and EtOH (65 mL) was heated to reflux for 3 h, cooled, concentrated and partitioned between EtOAc and H$_2$O. The EtOAc extract was washed with brine, dried (Na$_2$SO$_4$), filtered and concentrated in vacuo to afford 4.5 g (99%) of 52c as a white solid.

step 3—A solution of 52c (4.4 g, 12.3 mmol) and MeOH (25 mL)/H$_2$O (15 mL)/HCO$_2$H (15 mL) cooled in an ice-water bath was added portion wise over 1 h, Zn dust 1.61 g, 24.6 mmol). (S. Kukolja, et al., *J. Med. Chem.* 1985 28:1886) The solution was stirred at 0° C. for 7 h, removed from the ice bath and stirred an addition 2 h. TLC analysis of the mixture indicated only partial transformation occurred and another aliquot of Zn (0.8 g, 1, eq.) was added and the reaction stirred for 40 h at RT. The mixture was filtered through CELITE and the pad washed with MeOH. The filtrate was concentrated, dilute HCl was added and the solution was extracted with EtOAc. The EtOAc layer was washed with 1N NaOH, dried (Na$_2$SO$_4$), filtered and concentrated in vacuo. The crude product was purified by SiO$_2$ chromatography eluting with an EtOAc/hexane gradient (75 to 100% EtOAc) to afford 2.9 g (67%) of 54 as a white solid.

step 4—To a solution of 54 (2.7 g, 8.0 mmol) and DMF (50 mL) was added dimethoxymethyl-dimethyl-amine (1.42 g, 12 mmol) and the resulting solution stirred overnight at RT. The reaction mixture was concentrated in vacuo and finally subjected to a high vacuum for 2 h to afford 56 which used without additional purification.

step 5—To a solution of 56 (3.2 g, 8.0 mmol) and EtOH (25 mL) was added hydrazine (0.5 mL, 15.9 mmol) and the resulting solution was heated to reflux for 2 h. The solution was cooled to RT and concentrated in vacuo and purified by SiO$_2$ chromatography eluting with an EtOAc/hexane gradient (50 to 100% EtOAc) to afford 1.7 g (63%) of 58 as a white solid.

step 6—To a solution of 58 (1.0 g, 2.9 mmol) in CHCl$_3$ (7.5 mL) and MeOH (7.5 mL) was added NaOAc (0.29 g, 3.5 mmol) and the resulting solution cooled in an ice/MeOH bath. To this solution was added bromine (0.34 g, 2.2 mol) dropwise over 1 to 2 min. After approximately 1 min, starting material appeared to have been consumed (TLC) and the reaction was quenched with aq. Na$_2$CO$_3$ and extracted with CHCl$_3$. The combined extracts were dried (Na$_2$SO$_4$), filtered and concentrated in vacuo. The crude product was purified by SiO$_2$ chromatography eluting with an EtOAc/hexane gradient (50 to 100% EtOAc) to afford 0.58 g (77%) of 60 as a yellow solid.

step 7-Palladium-catalyzed coupling of 60 and 61 (CASRN 1132942-08-50) IS carried out in accord with the procedure described in step 7 of example 1. The crude product was purified by SiO$_2$ chromatography eluting with an EtOAc/hexane gradient (0 to 100% EtOAc) to afford 62.

Example 5

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from *E. coli* strain BL21(DE) pLysS. The construct, containing the coding sequence of HCV NS5B Con1 (GenBank accession number AJ242654) was inserted into the plasmid construct pET17b, downstream of a T7 promoter expression cassette and transformed into *E. coli*. A single colony was grown overnight as a starter culture and later used inoculate 10 L of LB media supplemented with 100 µg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 µl enzymatic reaction contained 20 nM RNA template derived from the complementary sequence of the Internal Ribosome Entry Site (cIRES), 20 nM NS5B570n-Con1 enzyme, 0.5 µCi of tritiated UTP (Perkin Elmer catalog no. TRK-412; specific activity: 30 to 60 Ci/mmol; stock solution concentration from 7.5×10−5 M to 20.6×10−6 M), 1 µM each ATP, CTP, and GTP, 40 mM Tris-HCl pH 8.0, 40 mM NaCl, 4 mM DTT (dithiothreitol), 4 mM MgCl2, and 5 µl of compound serial diluted in DMSO. Reaction mixtures were assembled in 96-well filter plates (cat #MADVNOB, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acid, 4 reaction volumes of 70% (v/v) ethanol, air dried, and 25 µl of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode Normal, Count Time: 1 min, Background Subtract: none, Cross talk reduction: Off).

Data was analyzed in Excel® (Microsoft) and Activity-Base® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% (IC$_{50}$) was calculated by fitting equation (i) to the data where "Y"

$$Y = \% \text{ Min} + \frac{(\% \text{ Max} - \% \text{ Min})}{\left[1 + \frac{X}{(IC_{50})^S}\right]} \quad (i)$$

corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

Example 6

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 μl of phosphate buffered saline (pH 7.0) (PBS) per well and lysed with 20 μl of 1×*R. luciferase* Assay lysis buffer prior to incubation at room temperature for 20 min. The plate was then inserted into the Centro LB 960 microplate luminometer (Berthold Technologies), and 100 μl of *R. luciferase* Assay buffer was injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE III

| Compound Number | HCV Replicon Activity $IC_{50}$ (μM) |
| --- | --- |
| I-1 | 0.0061 |
| I-4 | 0.0039 |

Example 7

Determination of Pharmacokinetic Parameters in Rats

Intact male IGS Wistar Han Rats Crl:WI(GLx/BRL/Han) IGS BR (Hanover-Wistar) rats weighing 200-250 g were used. Groups of three rats were used for each dose level of an experimental compound. Animals were allowed normal access to chow and water throughout the experiment. The test substance was formulated as an aqueous suspension containing Captex355EP, Capmul MCM, EtOH, and propylene glycol (30:20:20:30) at a dose equivalent to 10 mg/kg of the I-6 and was administered orally by gavage. A blood sample (0.3 mL) was collected from the treated rats at, 0.25, 0.5, 1, 3, 5, and 8 h from a jugular cannula and at 24 h by cardiac puncture. Potassium oxalate/NaF were added to the samples which were stored on ice during sampling procedure. The samples were spun in a refrigerated centrifuge at −4° C. as soon as possible and the plasma samples were stored in a −80° C. freezer until analysis. Aliquots of plasma (0.05 mL) were mixed with 0.1 mL of acetonitrile. Internal standard (0.05 mL in water) and 0.02 mL blank solvent were added. A set of calibration standards was prepared by mixing 0.05-mL aliquots of plasma from untreated rats with 0.1 mL acetonitrile, 0.02-mL aliquots of standard solution in methanol:water (1:1) and 0.05-mL aliquots of the internal standard in water. Each plasma sample and calibration standard was vortexed thoroughly and then centrifuged at 3000 rpm for 5 min to precipitate the protein. Supernatant (100 μL each) from centrifugation was transferred into a 96-well plate containing 200 μL of aqueous mobie phase for LC/MS/MS analysis.

TABLE IV

Summary of Pharmacokinetic Data

|  | I-3 | I-3 (non-deuterated) |
| --- | --- | --- |
| $C_{max}$ (ng/mL) | 83.4 | 55.8 |
| AUC (ng * h/mL) | 810 | 338 |
| $AUC_{0 \to 24}$ (ng * h/mL, extrapolated) | 1000 | 365 |

Example 8

Pharmaceutical compositions of the subject Compounds for administration via several routes were prepared as described in this Example.

| Composition for Oral Administration (A) | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
| --- | --- |
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
| --- | --- |
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I wherein:

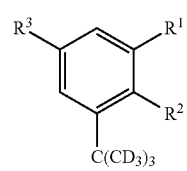
(I)

$R^1$ is CH=CHAr, C≡CAr, $[C(R^5)_2]_2$Ar or naphthyl wherein said naphthyl is optionally substituted with $[C(R^5)_2]_{0-3}NR^aR^b$;

Ar is phenyl or, pyridinyl or pyridazinyl wherein said phenyl and pyridinyl are Ar is optionally independently substituted with one to three substitutents selected from the group consisting of:
 (a) $[C(R^5)_2]_{0-3}NR^aR^b$,
 (b) $C_{1-10}$ hydroxyalkyl wherein one or two carbon atoms optionally can be replaced by oxygen provided that the replacement does not form a peroxide,
 (c) $C_{1-3}$ alkoxy-$C_{1-6}$ alkyl,
 (d) carboxyl,
 (e) $X^1[C(R^5)_2]_{1-6}CO_2R^4$ wherein $X^1$ is O, $NR^5$, or a bond and $R^4$ is hydrogen or $C_{1-6}$ alkyl,
 (f) $C_{1-6}$ alkoxycarbonyl,
 (g) halogen,
 (h) $[C(R^5)_2]_{0-3}CN$,
 (i) $C_{1-6}$ alkyl, and
 (j) $C_{1-6}$ haloalkyl;

$R^2$ is hydrogen, $C_{1-6}$ alkoxy, halogen or $C_{1-6}$ alkyl;

$R^3$ is

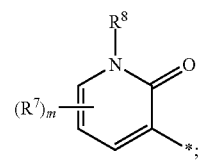
A-1

$R^5$ is independently in each occurrence hydrogen or $C_{1-3}$ alkyl;

$R^7$ is selected from the group consisting of:
 (a) halogen,
 (b) $C_{1-6}$ alkyl wherein one or two carbon atoms optionally can be replaced by oxygen provided that the replacement does not form a peroxide,
 (c) $C_{1-3}$ haloalkyl,
 (d) $C_{1-3}$ alkoxy,
 (e) $C_{2-6}$ hydroxyalkyl wherein one or two carbon atoms optionally can be replaced by oxygen provided that the replacement does not form a peroxide or a hemiacetal;
 (f) $NR^5[C(R^5)_2]$—$C_{2-6}$ hydroxyalkyl;
 (g) cyano-$C_{1-3}$ alkyl,
 (h) $X^2[C(R^5)_2]_{1-6}CO_2H$,
 (i) $[C(R^5)_2]_{1-6}NR^cR^d$, and
 (j) $X^2$—$[C(R^5)_2]_{2-6}NR^cR^d$ wherein $X^2$ is O or $NR^5$;

$R^8$ is hydrogen or $CH_2OR^9$ wherein $R^9$ is valine, proline or $P(=O)(OH)_2$;

$R^9$ is hydrogen or $C_{1-6}$ alkyl;

Y is hydrogen or hydroxyl;

m is zero or one;

R$^a$ and R$^b$ are (i) independently in each occurrence
- (a) hydrogen,
- (b) C$_{1-6}$ alkyl,
- (c) SO$_2$R$^6$ wherein R$^6$ is C$_{1-6}$ alkyl, C$_{1-6}$ haloalkyl, C$_{3-7}$ cycloalkyl, C$_{3-7}$ cycloalkyl-C$_{1-3}$ alkyl, C$_{1-6}$ alkoxy-C$_{1-6}$ alkyl or SO$_{2/Br}$[C(R$^5$)$_2$]$_{0-6}$NR$^c$R$^d$, or,
- (d) C$_{1-3}$ haloalkyl,
- (e) C$_{1-6}$ acyl,
- (f) carbamoyl,
- (g) C$_{1-3}$ alkylcarbamoyl, or,
- (h) C$_{1-3}$ dialkylcarbamoyl,
- (d) C$_{1-6}$ acyl,
- (e) carbamoyl,
- (f) C$_{1-3}$ alkylcarbamoyl, or
- (g) C$_{1-3}$ dialkylcarbamoyl, or (ii) R$^a$ and R$^b$ taken together with the nitrogen to which they are attached are an optionally substituted cyclic amine;

R$^c$ and R$^d$ are independently hydrogen or C$_{1-6}$ alkyl or R$^c$ and R$^d$ together with the nitrogen to which they are attached are an optionally substituted cyclic amine; or, a pharmaceutically acceptable salt thereof.

2. A compound according to claim 1 wherein R$^1$ is CH=CHAr.

3. A compound according to claim 2 wherein R$^2$ is C$_{1-6}$ alkoxy or hydrogen and Ar is phenyl substituted at the four-position by NR$^a$R$^b$ and optionally further substituted at one of the open positions.

4. A compound according to claim 3 where R$^a$ is hydrogen, R$^b$ is SO$_2$R$^6$ wherein R$^6$ is C$_{1-6}$ alkyl, C$_{3-7}$ cycloalkyl or C$_{3-7}$ cycloalkyl-C$_{1-3}$ alkyl and R$^7$ is C$_{1-6}$ alkyl, C$_{1-6}$ alkoxy or halogen and m is 1.

5. A compound according to claim 2 wherein Ar is either 2-pyridinyl substituted at the 5-position by NR$^a$R$^b$ or 3-pyridinyl substituted at the six-position by NR$^a$R$^b$, and the pyridine is optionally further substituted at one of the open positions, R$^a$ is hydrogen and, R$^b$ is SO$_2$R$^6$ and R$^6$ is C$_{1-6}$ alkyl, C$_{3-7}$ cycloalkyl or C$_{3-7}$ cycloalkyl-C$_{1-3}$ alkyl.

6. A compound according to claim 1 wherein R$^1$ is naphthalene.

7. A compound according to claim 6 where R$^1$ is 2-naphthalene substituted 6-position by NR$^a$R$^b$ wherein R$^a$ is hydrogen, R$^b$ is SO$_2$R$^6$, R$^2$ is C$_{1-6}$ alkoxy or hydrogen.

8. A compound according to claim 1 selected from the group consisting of:
- N-(4-{(E)-2-[3-[1,1-di(methyl-d3)ethyl-2,2,2-d3]-2-methoxy-5-(2-oxo-1,2-dihydro-pyridin-3-yl)-phenyl]-vinyl}-phenyl)-methanesulfonamide;
- N-(4-{(E)-2-[3-[1,1-di(methyl-d3)ethyl-2,2,2-d3]-2-methoxy-5-(6-methyl-2-oxo-1,2-dihydro-pyridin-3-yl)-phenyl]-vinyl}-phenyl)-methanesulfonamide; and,
- N-(4-{(E)-2-[3-[1,1-di(methyl-d3)ethyl-2,2,2-d3]-5-(5-chloro-2-oxo-1,2-dihydro-pyridin-3-yl)-2-methoxy-phenyl]-vinyl}-phenyl)-methanesulfonamide; or, a pharmaceutically acceptable salt thereof.

9. A compound according to claim 1 selected from the group consisting of:
- 2-{(E)-2-[3-[1,1-di(methyl-d3)ethyl-2,2,2-d3]-2-methoxy-5-(2-oxo-1,2-dihydro-pyridin-3-yl)-phenyl]-vinyl}-5-methanesulfonylamino-benzoic acid methyl ester;
- 2-{(E)-2-[3-[1,1-di(methyl-d3)ethyl-2,2,2-d3]-5-(2-oxo-1,2-dihydro-pyridin-3-yl)-phenyl]-vinyl}-5-methanesulfonylamino-benzoic acid;
- N-(4-{(E)-2-[3-[1,1-di(methyl-d3)ethyl-2,2,2-d3]-2-methoxy-5-(2-oxo-1,2-dihydro-pyridin-3-yl)-phenyl]-vinyl}-3-hydroxymethyl-phenyl)-methanesulfonamide;
- N-(4-{(E)-2-[3-[1,1-di(methyl-d3)ethyl-2,2,2-d3]-2-methoxy-5-(2-oxo-1,2-dihydro-pyridin-3-yl)-phenyl]-vinyl}-3-methoxymethyl-phenyl)-methanesulfonamide;
- N-(6-{(E)-2-[3-[1,1-di(methyl-d3)ethyl-2,2,2-d3]-5-(5-chloro-2-oxo-1,2-dihydro-pyridin-3-yl)-2-methoxy-phenyl]-vinyl}-pyridin-3-yl)-methanesulfonamide;
- N-(5-{(E)-2-[3-[1,1-di(methyl-d3)ethyl-2,2,2-d3]-2-methoxy-5-(2-oxo-1,2-dihydro-pyridin-3-yl)-phenyl]-vinyl}-pyridin-2-yl)-methanesulfonamide;
- 5-methanesulfonylamino-pyridine-2-carboxylic acid [3-[1,1-di(methyl-d3)ethyl-2,2,2-d3]-2-methoxy-5-(2-oxo-1,2-dihydro-pyridin-3-yl)-phenyl]-amide;

a pharmaceutically acceptable salt thereof.

10. A method for treating a Hepatitis C Virus (HCV) infection comprising administering to a patient in need thereof, a therapeutically effective quantity of a compound according to claim 1.

11. The method of claim 10 further co-comprising administering at least one immune system modulator and/or at least one antiviral agent that inhibits replication of HCV.

12. The method of claim 11 wherein the immune system modulator is an interferon, interleukin, tumor necrosis factor or colony stimulating factor.

13. The method of claim 12 wherein the immune system modulator is an interferon or chemically derivatized interferon.

14. The method of claim 11 wherein the antiviral compound is selected from the group consisting of a HCV protease inhibitor, another HCV polymerase inhibitor, a HCV helicase inhibitor, a HCV primase inhibitor and a HCV fusion inhibitor.

15. A method for inhibiting replication of HCV in a cell by delivering a therapeutically effective amount of a compound according to claim 1.

16. A composition comprising a compound according to claim 1 admixed with at least one pharmaceutically acceptable carrier, diluent or excipient.

* * * * *